US00PP21121P2

(12) United States Plant Patent
Klemm et al.

(10) Patent No.: US PP21,121 P2
(45) Date of Patent: Jun. 29, 2010

(54) ***OSTEOSPERMUM* PLANT NAMED 'KLEOE08161'**

(50) Latin Name: *Osteospermum ecklonis*
Varietal Denomination: KLEOE08161

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,376

(22) Filed: Mar. 24, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Susan B McCormick Ewoldt
(74) *Attorney, Agent, or Firm*—Jondle & Associates, P.C.

(57) ABSTRACT

An *Osteospermum* cultivar named 'KLEOE08161' particularly distinguished by deep yellow-orange inflorescences, umbrella-type flowers with narrow-shaped petals, and a compact growth habit, is disclosed.

1 Drawing Sheet

Genus and species: *Osteospermum ecklonis.*
Variety denomination: 'KLEOE08161'.

BACKGROUND OF THE NEW PLANT

The present invention comprises a new and distinct cultivar of *Osteospermum*, botanically known as *Osteospermum ecklonis*, and hereinafter referred to by the cultivar name 'KLEOE08161'. The new cultivar originated from an open-pollination made in July 2005 in Stuttgart, Germany. The female parent was a proprietary un-named *Osteospermum* plant (unpatented), and the male parent was an un-named *Osteospermum* plant (unpatented). The seeds produced by the open-pollination were sown in Spring 2006. A single plant selection was chosen for further evaluation and for asexual propagation in Spring 2006.

The new cultivar was created in 2005 in Stuttgart, Germany, and has been asexually reproduced repeatedly by vegetative cuttings in Stuttgart, Germany over a two and one-half year period. The present invention has been found to retain its distinctive characteristics through successive asexual propagations.

Plant Breeder's Rights for this cultivar have been applied for in Switzerland on Aug. 5, 2008 and in Canada on Mar. 31, 2008. 'KLEOE08161' has not been made publicly available more than one year prior to the filing date of this application.

SUMMARY OF THE INVENTION

The following are the most outstanding and distinguishing characteristics of the new cultivar when grown under normal horticultural practices in Stuttgart, Germany.

1. Deep yellow-orange inflorescences;
2. Umbrella-type flowers with narrow-shaped petals; and
3. A compact growth habit.

DESCRIPTION OF THE PHOTOGRAPH

This new *Osteospermum* plant is illustrated by the accompanying photograph which shows blooms, buds, and foliage of the plant; the colors shown are as true as can be reasonably obtained by conventional photographic procedures.

The photograph is of a plant about 4 to 5 months old taken in Summer 2008 and in the field in Stuttgart, Germany under conditions which approximate those generally used in commercial practice.

DESCRIPTION OF THE NEW CULTIVAR

The following detailed descriptions set forth the distinctive characteristics of 'KLEOE08161'. The data which define these characteristics were collected from asexual reproductions carried out in Stuttgart, Germany. The plant history was taken on plants about 4 to 5 months old, grown in the field. The plants were pinched once at 12 weeks. Color readings were taken under natural light. Color references are primarily to the R.H.S. Colour Chart of The Royal Horticultural Society of London (R.H.S.) (2001).

DESCRIPTION OF THE NEW PLANT

Classification:
- *Family.*—Asteraceae.
- *Botanical name.*—*Osteospermum ecklonis.*
- *Common name.*—African daisy.

Parentage:
- *Female parent.*—A proprietary un-named Osteospermum plant (unpatented).
- *Male parent.*—An un-named *Osteospermum* plant (unpatented).

Plant:
- *Growth and branching habit.*—Semi-upright.
- *Height (from top of soil, including inflorescence).*—30.0 cm.
- *Width (including inflorescences).*—40.0 cm.
- *Propagation.*—Cuttings.
- *Time to produce a finished flowering plant.*—10 weeks.
- *Time to initiate and develop roots.*—4 weeks.
- *Root description habit.*—Freely rooting.

Leaves:
- *Arrangement.*—Arranged in a whorl.
- *Shape.*—Dentiform.
- *Apex.*—Obtuse.

*Base.*—Acute.
*Margin.*—Serrated, small-medium indentations for immature leaves and deep indentations for mature leaves.
*Texture* (*both surfaces*).—Rough (immature and mature leaves).
*Immature leaf.*—Color (upper and lower surfaces): RHS 146A.
*Mature leaf.*—Color: Upper surface: RHS 147A. Lower surface: RHS 147B.
*Length.*—5.0 cm to 6.0 cm (mature leaf) and 2.0 cm to 3.0 cm (immature leaf).
*Width.*—2.0 cm to 3.0 cm (mature leaf) and 0.2 cm to 0.5 cm (immature leaf).
*Petioles.*—Absent.
*Venation pattern.*—Pinnate.

Stems:
*Total number of branches.*—7.
*Length.*—30.0 cm.
*Diameter.*—0.2 cm to 0.3 cm.
*Internode length.*—2.0 cm.
Color.—RHS 146C.
*Texture.*—Leathery at the base and rough at the apex.
*Anthocyanin.*—Absent.

Inflorescence buds:
*Shape.*—Ovate.
*Diameter.*—0.7 cm.
*Length.*—2.5 cm.
*Color* (*at tight bud just before the ray florets unfold*).—RHS 144A and RHS 144B.

Inflorescence:
*Type.*—Single.
*Blooming habit.*—Plants flower continuously from Spring to Fall given the proper growing conditions.
*Quantity of inflorescences per plant.*—30 to 35.
*Lastingness of the inflorescences on the plant.*—7 to 10 days.
*Fragrance.*—Absent.
*Inflorescence diameter.*—6.0 cm to 7.0 cm.
*Inflorescence depth.*—Variable throughout flower development.
*Disc diameter.*—6.0 cm to 7.0 cm.

Disc floret: Absent.

Ray floret:
*Quantity per inflorescence.*—15.
*Shape.*—Lanceolate.
*Color.*—Upper surface: RHS 17A and RHS 45A (ring around the disc). Lower surface: RHS 187A and RHS 187B.
*Length.*—3.5 cm.
*Width.*—1.8 cm.
*Apex.*—Obtuse.
*Base.*—Acute.
*Margin.*—Entire.
*Texture.*—Smooth.
*Peduncle.*—Length: 3.5 cm. Diameter: 0.1 cm. Texture: Rough. Color: RHS 143A and RHS 143B.

Phyllaries:
*Arrangement.*—Single.
*Observed quantity per plant.*—15.
*Shape.*—Lanceolate.
*Color.*—Upper surface: RHS 143A and RHS 143B and RHS 187A at the apex. Lower surface: RHS 144A and RHS 144B.
*Length.*—2.0 cm.
*Width.*—0.2 cm.
*Apex.*—Acute.
*Base.*—Truncate.
*Margin.*—Entire.
*Texture.*—Rough.

Reproductive organs:
*Androecium.*—Stamens: Stamen quantity: Some, not possible to quantify. Stamen shape: Filamentous. Stamen color: RHS 6A. Filament length: 2.1 cm. Filament diameter: 0.001 cm. Anther: Shape: Elliptic. Color: RHS 200A. Length: 0.3 cm. Diameter: 0.1 cm. Pollen: Pollen color: RHS 14A. Pollen amount: Moderate/sparse.
*Gynoecium.*—Pistils: Number: Greater than 15. Pistil length: 1.6 cm. Diameter: 0.001 cm. Stigma: Stigma color: RHS 200A. Shape: Ovate. Length: 0.1 cm. Diameter: 0.001 cm. Style: Style color: RHS 155A. Style length: 1.5 cm. Diameter: 0.001 cm. Shape: Filamentous.

Fruit and seed set: None observed.

Disease and insect resistance: No particular disease or insect resistance observed.

COMPARISON WITH COMMERCIAL CULTIVAR

'KLEOE08161' differs from the commercial cultivar 'KLEOE06150' (U.S. Plant patent application Ser. No. 12/055,096, now abandoned) in that 'KLEOE08161' has darker yellow-orange inflorescences than 'KLEOE06150' (U.S. Plant patent application Ser. No. 12/055,096, now abandoned).

I claim:

1. A new and distinct cultivar of *Osteospermum* plant named 'KLEOE08161' as shown and described herein.

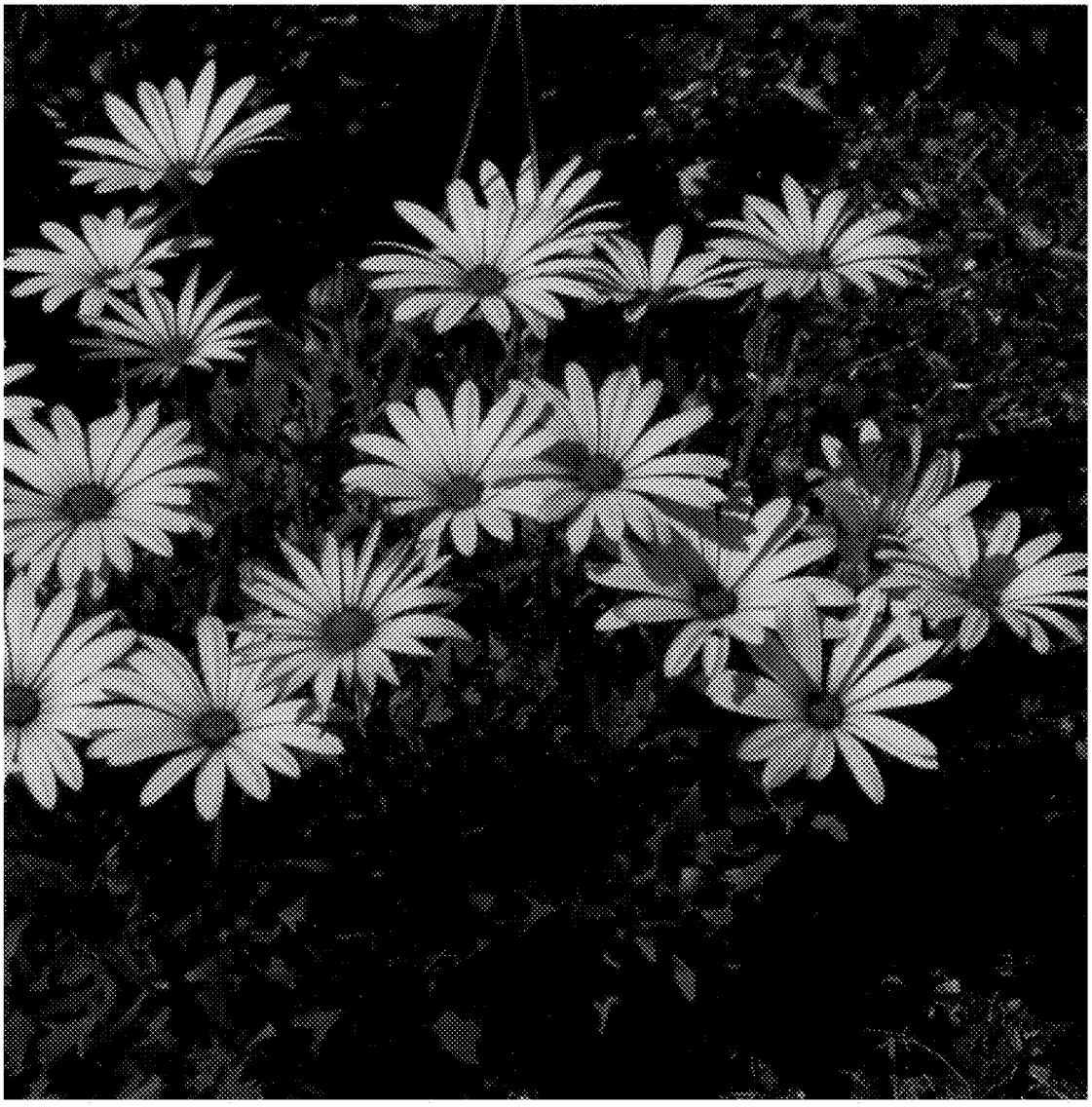

* * * * *